United States Patent [19]
Bucalo

[11] 3,934,575
[45] Jan. 27, 1976

[54] TAMPON DEVICE TO TEST FOR MICRO-ORGANISMS

[76] Inventor: Louis Bucalo, 155 Roberts St., New York, N.Y. 11741

[22] Filed: Aug. 23, 1974

[21] Appl. No.: 499,925

Related U.S. Application Data

[62] Division of Ser. No. 329,862, Feb. 5, 1973, Pat. No. 3,842,166.

[52] U.S. Cl. ............... 128/2 W; 128/270; 195/139; 424/9
[51] Int. Cl.² ......................................... A61B 10/00
[58] Field of Search .......... 128/2 W, 2 B, 269, 270; 195/139, 140; 424/9

[56] References Cited
UNITED STATES PATENTS

| | | | |
|---|---|---|---|
| 2,301,868 | 11/1942 | Gurley, Jr. et al. | 128/270 X |
| 2,905,169 | 9/1959 | Nieburgs | 128/2 B |
| 3,086,527 | 4/1963 | Forrest | 128/2 W X |
| 3,282,114 | 11/1966 | Pell | 128/2 W X |
| 3,368,549 | 2/1968 | Barr et al. | 128/2 W |
| 3,386,441 | 6/1968 | De Merre | 128/284 |
| 3,509,872 | 5/1970 | Truhan | 128/2 W |
| 3,589,983 | 6/1971 | Holderith et al. | 195/139 |
| 3,817,839 | 6/1974 | Warren | 195/139 X |
| R24,666 | 7/1959 | Draghi | 128/2 W |

FOREIGN PATENTS OR APPLICATIONS

349,885  6/1931  United Kingdom ................ 128/270

*Primary Examiner*—Kyle L. Howell
*Attorney, Agent, or Firm*—Steinberg and Blake

[57] ABSTRACT

For use in testing for the presence of micro-organisms, a tampon, and a plurality of devices incorporated therein, said devices each include a culture medium for promoting the growth of micro-organisms and a carrier means for carrying the culture medium.

5 Claims, 5 Drawing Figures

U.S. Patent  Jan. 27, 1976  3,934,575
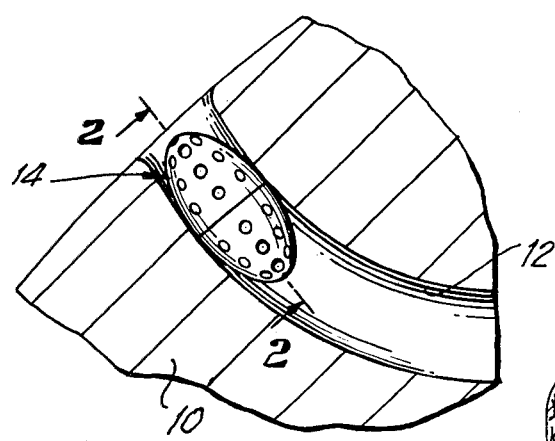
FIG.1
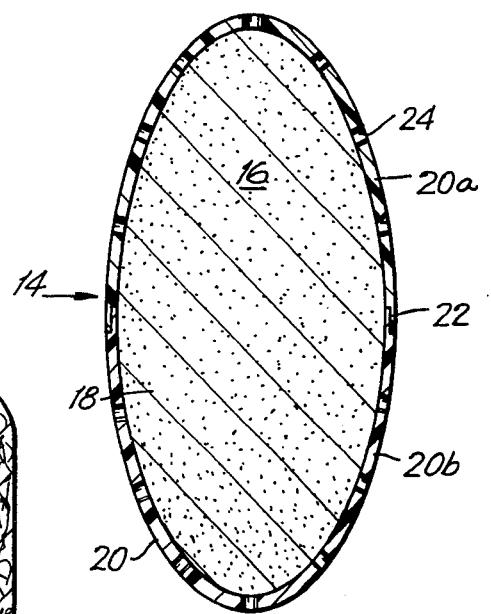
FIG.2
FIG.5
FIG.3
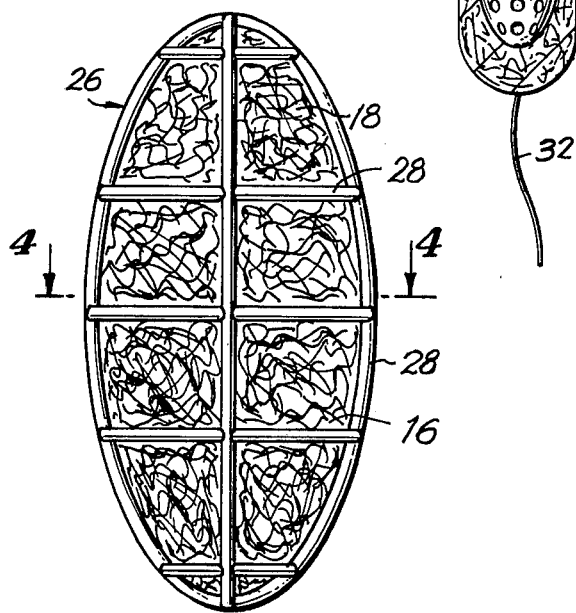
FIG.4
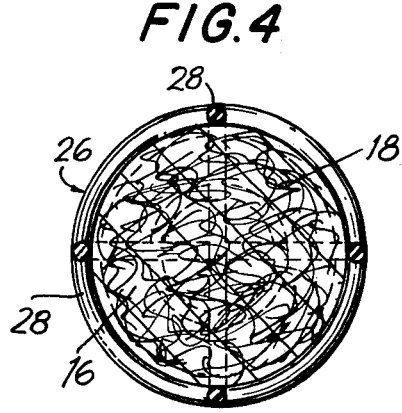

TAMPON DEVICE TO TEST FOR MICRO-ORGANISMS

CROSS REFERENCE TO RELATED APPLICATION

This application is a division of copending application Ser. No. 329,862, filed Feb. 5, 1973, and entitled "Method and Device for Testing for the Presence of Micro-Organisms" now U.S. Pat. No. 3,842,166.

BACKGROUND OF THE INVENTION

The present invention relates to devices for testing for the presence of micro-organisms.

At the present time, in order to determine whether or not a patient suffers from certain meladies, a physician will take a swab and apply it to an area of the body where the presence of micro-organisms is suspected, removing a smear from the suspected area and applying to a culture medium which is then incubated in a suitable incubator for a period of time so as to determine whether or not the suspected micro-organisms are indeed present. Thus, the physician will apply the swab to the ear, nose, throat, vagina, or the like, and will then apply a smear to the culture medium which is normally supported in a suitable dish. After the smear is applied to the surface of the culture medium, the dish with the medium is placed in the incubator, and after a given incubation period at a predetermined temperature the culture medium is inspected to determine whether or not there has been growth of the suspected micro-organisms.

Thus, with the above conventional procedures it is essential to carry out the steps of applying the swab to the area which is suspect, transferring a smear to the culture medium, and an incubator is required to receive the culture medium.

These procedures are relatively involved, create a certain amount of discomfort to the patient, and require the use of equipment such as an incubator. Very often a physician does not have an incubator available for his own use and must send the swab with the smear thereon to a laboratory where the incubation is carried out. The laboratory will then inform the physician of the result of the incubation.

In addition to the disadvantages resulting from the time and inconvenience as well as the equipment required for the above conventional procedures, there is always the possibility that an incorrect diagnosis is made. For example, it may happen that the micro-organisms are thriving in the body of a patient whereas in the transfer of the smear to the culture medium and in the incubation thereof the conditions for growth of the micro-organisms are different from that which prevails in the body, so that even though a negative result is indicated after incubation, nevertheless micro-organisms may still be present unknown to the physician because the conditions for growth in the incubator are not the same as in the body and improper diagnosis results. Moreover, because of the delay encountered with the above procedures it often is not possible to treat a patient as soon as is desirable. The result is that for safety purposes patients will sometimes be treated for diseases whch they actually do not have.

SUMMARY OF THE INVENTION

It is accordingly a primary object of the present invention to provide a device which will avoid the above drawbacks.

In particular, it is an object of the invention to provide a device which will eliminate the need for an incubator.

In addition, it is an object of the present invention to provide a device which will eliminate the necessity for transferring with a swab a smear from a suspected area of a patient to a culture medium.

Furthermore, it is an object of the present invention to provide a an apparatus which will enable the presence of micro-organisms to be detected under the very same conditions as those prevailing in the body of a patient.

In addition, it is an object of the present invention to provide a device which will enable tests for the presence of micro-organisms to be carried out in a simple, inexpensive, highly convenient manner directly by an attending physician without requiring the use of the facilities of a laboratory. Thus, it becomes possible with the present invention to avoid any delays such as those involved in mailing specimens to a laboratory to test it.

According to the invention a culture medium is introduced directly into a body cavity where it is suspected that micro-organisms may be present. This culture medium is permitted to remain in the body cavity for a period of time which is sufficient to indicate growth of the micro-organisms if indeed they are present. After this latter period of time has elapsed the culture medium is removed from the body cavity and examined so that an accurate diagnosis can be conveniently made in as short a time as possible.

The device of the invention includes a culture medium which is carried by a carrier means which together with the culture medium has a size and configuration enabling the device to be comfortably and conveniently introduced into a body cavity to remain temporarily therein for the time required for the micro-organisms, if any, to grow at the culture medium, so that after removal of the device it can be examined to make an accurate diagnosis.

BRIEF DESCRIPTION OF DRAWINGS

The invention is illustrated by way of example in the accompanying drawings which form part of this application and in which:

FIG. 1 is a schematic illustration of a device of the invention situated in a body cavity;

FIG. 2 is a sectional elevation, on an enlarged scale as compared to FIG. 1, of the device of FIG. 1 taken along line 2—2 of FIG. 1 in the direction of the arrows;

FIG. 3 is an elevation of another possible embodiment of a device according to the invention;

FIG. 4 is a sectional plan view of the device of FIG. 3 taken along line 4—4 of FIG. 3 in the direction of the arrows; and FIG. 5 is a schematic representation of the manner in which the device of the invention may be incorporated into a tampon, according to a further feature of the invention.

DESCRIPTION OF PREFERRED EMBODIMENTS

In accordance with the present invention, instead of obtaining a smear from a part of the body where it is suspected that micro-organisms are present and placing the smear on a culture medium which is then incubated, the culture medium is placed directly in the body cavity at the area where the presence of the micro-organisms is suspected, and after a time normally required for growth of the micro-organisms, if any, the device of the invention is removed from the body cavity and examined so as to diagnose whether or not there are indeed micro-organisms present at the body cavity. In this way it becomes unnecessary to use incubators, to transfer a smear to a culture medium, and the diagnosis is made as rapidly as possible and as accurately as possible since the growth of the micro-organisms, if any, takes place directly in the body under precisely the same conditions which prevail in the body of the patient.

Thus, referring to FIG. 1, there is schematically illustrated therein a part 10 of the body of a human being, this part 10 having the body cavity 12. This schematically illustrated body cavity 12 may be any cavity of the body such as the mouth, the nose, a sinus passage, the ear, the anal canal, the vagina, the urethra, the uterus, etc.

Assuming that a physician suspects a given area of the body as being infected by a micro-organism, the physician will simply introduce into the body cavity where the presence of infection is suspected a device 14 according to the present invention. This device 14 includes a culture medium 16 (FIG. 2) which may be any known culture medium which will promote the growth of micro-organisms if the latter are present. Since such micro-organisms normally are not capable of retaining a given shape and size, the culture medium 16 is carried by a carrier means which includes a body 18 of compressed filamentary material and an outer frame 20 which carries the compressed body 18 of filamentary material. This body of filamentary material 18 may be compressed cotton fibers, fine gold wire filament, or any fine plastic monofilaments such as nylon or polyester filaments which when compressed form a large surface area having a large number of interstices in which the nutrient or culture medium 16 will become located. The frame 20 forms a shell which surrounds the body of compressed filamentary material 18 to retain the latter in its compressed condition. This frame 20 in the example of FIG. 2 includes a pair of receptacles portions 20a and 20b joined together at their mating flanges 22 and releasably held together for example by gluing these flanges to each other if desired. The walls of the shell 20a and 20b are formed with a large number of openings 24 through which the micro-organisms will have free access to the culture medium 16.

In the embodiment of FIGS. 3 and 4, in order to expose as large an area as possible of the culture medium, the compressed body 18 of filamentary material which supports and carries directly the culture medium 16 is situated within and surrounded by a frame 26 made up of a number of intersecting ribs 28 which provide the relatively large open spaces indicated in FIGS. 3 and 4 so that the culture medium is almost entirely exposed at the outer surface of the compressed body of filamentary material 18.

According to the embodiment of FIG. 5, which is particularly adapted for use in testing for gonorrhea or vaginitis, the device of the invention such as that of FIG. 2 or that of FIG. 3 is incorporated into a tampon 30 of the type which is normally inserted into the vagina during the mentrual cycle, this tampon 30 having the string 32 which enables it to be conveniently removed. Thus, FIG. 5 shows a pair of the devices 14 incorporated into the tampon 30 which may then be conveniently introduced into the vagina to remain therein for a period of time sufficient to permit micro-organisms if they are present to grow at the culture medium in the devices 14. Then the tampon 30 is removed and the physician may examine the devices 14 to determine whether or not micro-organisms are present.

With respect to the devices of FIGS. 2 and 3, the outer frame such as the frame 20 of FIG. 2 or the frame 26 of FIG. 3 may be made of any metal or plastic compatible with the human body. The compressed body of filamentary material may be made of any of the filamentary materials referred to above or combinations thereof, or in fact any filamentary material compatible with the human body.

Examples of suitable culture mediums are as follows:

EXAMPLE 1

The following constitutes a diagnostic medium for determining the presence of *candida albicans* in vaginal infection. This basic medium is made antibacterial by the addition thereto of neomycin sulfate.

A medium is made of the following composition:

| | |
|---|---|
| Yeast Extract | 0.1% |
| Glycine | 1.0% |
| Dextrose | 1.0% |
| Bismuth Sulfite Indicator | 0.8% |
| Neomycin Sulfate | 0.0002% |
| Agar | 2.0% |
| Water q.s. | 100.0% |

When *C. Albicans* is present black colonies appear, while any other fungus will not give this type of growth. Bacteria are inhibited by both the Neomycin Sulfate and Bismuth Sulfite Indicator.

EXAMPLE 2

For identifying Alpha and Beta Hemolytic

| | |
|---|---|
| Beef Heart Infusion | 500 gm. |
| Tryptose | 10 gm. |
| Sodium Chloride | 5 gm. |
| Agar | 20 gm. |
| Water, q.s. | 1000 ml. |

EXAMPLE 3

For detecting bacterial growth in urine:

| | |
|---|---|
| Peptone | 10 gm. |
| Lactose | 5 gm. |
| Sucrose | 5 gm. |
| Dipotassium Phosphate | 2 gm. |
| Agar | 20 gm. |
| Eosin Y | 0.4 gm. |
| Methylene Blue | .065 gm. |
| Water, q.s. | 1000 ml. |

This shows a green metallic sheet with *E. Coli*.

EXAMPLE 4

For indentifying Staphylococci:

110 Media

| | |
|---|---|
| Yeast Extract | 2.5 gm. |
| Tryptose | 10.gm. |
| Gelatin | 30 gm. |
| Lactose | 2 gm. |

-continued

110 Media

| | |
|---|---|
| d-Mannitol | 10 gm. |
| Sodium Chloride | 75 gm. |
| Dipotassium Phosphate | 5 gm. |
| Agar | 20 gm. |
| Water, q.s. | 1000 ml. |

EXAMPLE 5

For indentifying Proteus:

Urea-Agar Base

| | |
|---|---|
| Peptone | 1 gm. |
| Dextrose | 1 gm. |
| Sodium Chloride | 5 gm. |
| Monopotassium Phosphate | 2 gm. |
| Urea | 20 gm. |
| Phenol Red | .012 gm. |
| Agar | 20 gm. |
| Water, q.s. | 1000 ml. |

Thus, with any suitable culture medium, such as those in the examples above, it is possible for the physician utilizing the device of the present invention, simply to introduce the device directly into the body cavity where it is suspected that the micro-organisms are present. The device is permitted to remain in the body cavity for the period of time required for growth of the micro-organism, if indeed it is present, and thereafter the physician will remove the device of the invention and will examine it so as to determine whether or not micro-organisms are indeed present. Since the device of the invention is incorporated directly into the body cavity to remain there at body temperature and under the exact conditions prevailing in the body, ideal conditions for growth of micro-organisms, if they are present, are used, and thus a far more accurate diagnosis is possible with the present invention than with conventional techniques and apparatus. In addition, any physician can readily practice the method of the invention without requiring the use of special equipment, laboratories, or the like, so that not only is there a great convenience and high accuracy in the diagnosis, but in addition there is a minimum of delay in making the diagnosis.

In any of the above devices, the culture medium may be divided into several sections for indicating, respectively, the presence of different micro-organisms, so that a broad spectrum type of differential devices is utilized for simultaneously growing a number of different culture. Also, in the case of the tampon, the devices incorporated therein may have, respectively, different culture mediums for indicating the presence of different micro-organisms.

What is claimed is:

1. For use in testing for the presence of micro-organisms, a tampon of a type which could be inserted into the vagina during the menstrual cycle, and at least one device embedded within and surrounded by the tampon, said device including a culture medium for promoting the growth of micro-organisms and a carrier means carrying the culture medium and rendering the latter accessible to fluids absorbed by the tampon for growing in the culture medium micro-organisms present in the fluids.

2. The combination of claim 1 and wherein a plurality of said devices are embedded within and surrounded by the said tampon.

3. The combination of claim 2 and wherein the culture mediums of said plurality of devices respectively have different compositions indicating the presence of different micro-organisms.

4. The combination of claim 2 and wherein said plurality of devices are longitudinally distributed along said tampon.

5. The combination of claim 1 and wherein the carrier means includes a compressed body of filamentary material surrounded by the culture medium and having the latter situated in interstices within the compressed body of filamentary material and said carrier means further including an outer frame surrounding and holding the compressed body of filamentary material and the culture medium and formed with openings through which micro-organisms will have free access to the culture medium.

* * * * *